United States Patent
Chorghade et al.

(10) Patent No.: US 7,038,073 B2
(45) Date of Patent: May 2, 2006

(54) SYNTHESIS OF 2-ALKYL AMINO ACIDS

(75) Inventors: Mukund S. Chorghade, Natick, MA (US); Mukund K. Gurjar, Pune Maharashtra (IN); Bhanu M. Chanda, Pune Maharashtra (IN)

(73) Assignee: Genzyme Corporation, Cambridge, MA (US)

( * ) Notice: Subject to any disclaimer, the term of this patent is extended or adjusted under 35 U.S.C. 154(b) by 79 days.

(21) Appl. No.: 10/439,265

(22) Filed: May 15, 2003

(65) Prior Publication Data

US 2004/0006224 A1 Jan. 8, 2004

Related U.S. Application Data

(60) Provisional application No. 60/392,833, filed on Jun. 27, 2002, provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002, provisional application No. 60/380,880, filed on May 15, 2002.

(51) Int. Cl.
*C07C 321/00* (2006.01)

(52) U.S. Cl. .................. 560/9; 560/12; 560/19
(58) Field of Classification Search ............ 560/9, 560/12, 19; 548/968, 966
See application file for complete search history.

(56) References Cited

U.S. PATENT DOCUMENTS

| | | | |
|---|---|---|---|
| 4,406,905 A | 9/1983 | Zähner et al. | |
| 5,554,753 A | 9/1996 | O'Donnell et al. | |
| 5,840,739 A | 11/1998 | Bergeron, Jr. | |
| 5,872,259 A | 2/1999 | Reuter | |
| 5,929,232 A | 7/1999 | Jacobsen et al. | |
| 5,929,252 A * | 7/1999 | Sharpless et al. | 548/968 |
| 6,083,966 A | 7/2000 | Bergeron, Jr. | |
| 6,159,983 A | 12/2000 | Bergeron, Jr. | |
| 6,383,233 B1 | 5/2002 | Reuter | |
| 6,428,583 B1 | 8/2002 | Reuter | |
| 6,521,652 B1 | 2/2003 | Bergeron | |
| 6,525,080 B1 | 2/2003 | Bergeron | |
| 6,559,315 B1 | 5/2003 | Bergeron | |
| 2003/0088105 A1 | 5/2003 | Krich et al. | |
| 2003/0220504 A1 | 11/2003 | Chorghade et al. | |
| 2003/0225287 A1 | 12/2003 | Chorghade et al. | |
| 2003/0229231 A1 | 12/2003 | Chorghade et al. | |
| 2003/0236404 A1 | 12/2003 | Gimi et al. | |
| 2003/0236426 A1 | 12/2003 | Chorghade et al. | |
| 2003/0236434 A1 | 12/2003 | Gimi et al. | |
| 2003/0236435 A1 | 12/2003 | Gimi et al. | |
| 2004/0002613 A1 | 1/2004 | Chorghade et al. | |
| 2004/0024224 A1 | 2/2004 | Chorghade et al. | |

FOREIGN PATENT DOCUMENTS

| | | |
|---|---|---|
| DE | 20 20 866 A | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |

OTHER PUBLICATIONS

Larsson et al., Acta Chemica Scandinavica, 1994, 48(6), pp. 511-516.*
Baldwin et al., Tetrahedron, 1993, 49:6309-6330.*
Baldwin et al., Journal of the Chemical Society, Chemical Communication, 1989, 23:1852-1854.*
Kogami et al., Bulletin of the Chemical Society of Japan, 1987, 60(8):2963-2965.*
Evans, D.A., et al., "Development of the Copper-Catalyzed Olefin Aziridination Reaction," *J. Am. Chem. Soc.*, 116: 2742-2753 (1994).
Evans, D.A., et al., "Bis(oxazoline)-Copper Complexes as Chiral Catalysts for the Enantioselective Aziridination of Olefins," *J. Am. Chem. Soc.*, 115:5328-5329 (1993).
Johnson, J. S., et al., "Chiral Bis(oxazoline) Copper (II) Complexes: Versatile Catalysts for Enantioselective Cycloaddition, Aldol, Michael, and Carbonyl Ene Reactions," *Acc. Chem. Res.*, 33:325-335 (2000).
Langham, C., et al., "Heterogeneous aziridination of alkenes using $Cu^{2+}$ exchanged zeolites," *Applied Catalysis A: General*, 182:85-89 (1999).
Langham, C., et al., "Catalytic asymmetric heterogeneous aziridination of alkenes using zeolite CuHY with [N-(p-tolylsulfony)imino]phenyliodinane as nitrene donor," *J. Chem. Soc., Perkin Trans.* 2:1043-1049 (1999).

(Continued)

*Primary Examiner*—Taofiq Solola
*Assistant Examiner*—Robert Shiao
(74) *Attorney, Agent, or Firm*—Hamilton, Brook, Smith, Reynolds, P.C.

(57) ABSTRACT

A method of preparing a 2-alkyl amino acid involves the aziridination of an alkylacrylate and the opening of the aziridine ring by addition of a side chain. This method can result in the preparation of enantiomeric excess of a 2-alkyl amino acid. The invention also discloses a method of preparing a class of iron chelating agents related to desferrithiocin, all of which contain a thiazoline ring. In this method, an aryl nitrile or imidate is condensed with cysteine, a 2-alkyl cysteine, or a cysteine ester.

19 Claims, No Drawings

OTHER PUBLICATIONS

Langham, C., et al., "Catalytic heterogeneous aziridination of alkenes using microporous materials," *Chem. Commun.*, 1601-1602 (1998).

Gullick, J., et al., "Aziridination of styrene: comparison of [N-(p-tolylsulfonyl)imino]phenyliodinane and chloramine-T as nitrene donors," *Journal of Molecular Catalysts A: Chemical*, 180:85-89 (2002).

Gullick, J., et al., "Heterogeneous catalytic aziridination of styrene using transition-metal-exchanged zeolite Y," *Catalysis Letters*, 75(3-4):151-154 (2001).

Taylor, S., "Catalytic asymmetric heterogeneous aziridination of styrene using CuHY: effect of nitrene donor on enantioselectivity," *J. Chem. Soc., Perkin Trans.*, 2:1714-1723 (2001).

Fuji, K., et al., "A New Access to Chiral Aziridines by Enzymatic Transesterification of *Meso*-Bis(Acetoxymethyl) Aziridines," *Tetrahedron Letters*, 31(46):6663-6666 (1990).

Ittah, Y., et al., "A New Aziridine Synthesis from 2-Azido Alcohols and Tertiary Phosphines. Preparation of Phenanthrene 9, 10-Imine," *J. Org. Chem.*, 43(22):4271-4273 (1978).

Konsler, R. G., et al., "Cooperative Asymmetric Catalysis with Dimeric Salen Complexes," *J. Am. Chem. Soc.*, 120: 10780-10781 (1998).

Annis, D. A., et al., "Polymer-Supported Chiral Co(Salen) Complexes: Synthetic Applications and Mechanistic Investigations in the Hydrolytic Kinetic Resolution of Terminal Epoxides," *J. Am. Chem. Soc.*, 121:4147-4154 (1999).

Senanayake, C. H. and Jacobsen, E. N., "Chiral (Salen)Mn (III) Complexes in Asymmetric Epoxidations: Practical Synthesis of cis-Aminoindanol and Its Application to Enantiopure Drug Synthesis," in Process Chemistry in the Pharmaceutical Industry, Gadamasetti, K. G., Ed., Dekker: New York, 1999, pp. 347-368.

Myers, J. K., et al., "Asymmetric Synthesis of β-Amino Acid Derivatives via Catalytic Conjugate Addition of Hydrazolic Acid to Unsaturated Imides," *J. Am. Chem. Soc.*, 121:8959-8960 (1999).

Jacobsen, E. N. and Wu, M. H., "Ring Opening of Epoxides and Related Reactions," in Comprehensive Asymmetric Catalysis, Jacobsen, E. N., Pfaltz, A. and Yamamoto, H., Eds., Springer: New York, 1999, pp. 1309-1326.

Jacobsen, E. N., "Aziridination," in Comprehensive Asymmetric Catalysis, Jacobsen, E. N., Pfaltz, A. and Yamamoto, H., Eds., Springer: New York, 1999, pp. 607-618.

Jacobsen, E. N., "Future Perspectives in Asymmetric Catalysis," in Comprehensive Asymmetric Catalysis, Jacobsen, E. N., Pfaltz, A. and Yamamoto, H., Eds., Springer: New York, 1999, pp. 1473-1477.

Li, Z., et al., "Enantioselective Ring Opening of Meso Aziridines Catalyzed by Tridentate Schiff Base Chromium (III) Complexes," *Organic Letters*, 1(10):1611-1613 (1999).

Schaus, S. E., et al., "Asymmetric Ring Opening of Meso Epoxides with TMSCN Catalyzed by (pybox)lanthanide Complexes," *Organic Letters*, 2(7):1001-1004 (2000).

Brandes, B. D., Regioselective Ring Opening of Enantiomerically Enriched Epoxides via Catalysis with Chiral (Salen)Cr(III) Complexes, *Synlett*, 1013-1015 (2001).

Gurjar, M. K., "Kinetic Resolution of Aryl Glycidyl Ethers: A Practical Synthesis of Optically Pure β-Blocker—S-Metoprolol," *Heterocycles*, 48(7):1471-1476 (1998).

Gurjar, M. K., "A Practical Synthesis of (R)-(-)-Phenylephrine Hydrochloride," *Organic Process Research & Development*, 2:422-424 (1998).

Chorghade, M.S., et al., "Synthesis of (2S,5S)-trans-S-(4-fluorophenoxymethyl)-2-(1-N-hydroxy ureidyl-3-butyn-4-yl)-tetrahydrofuran-(CMI-977)," *Pure Appl. Chem.*, 71(6): 1071-1074 (1999).

Joshi, R. A., et al., "A New and Improved Process for Celiprolol Hydrochloride," *Organic Process Research & Development*, 5(2):176-178 (2001).

Gurjar, M. K., et al., "A novel and simple asymmetric synthesis of CMI-977 (LDP-977): a potent anti-asthmatic drug lead," *Tetrahedron: Asymmetry*, 14:1363-1370 (2003).

Yasuhara, A., et al., "Deprotection of *N*-Sulfonyl Nitrogen-Heteroaromatics With Tetrabutylammonium Fluoride," *Tetrahedron Letters*, 39:595-596 (1998).

Maligres, P. E., et al., "Nosylaziridines: Activated Aziridine Electrophiles," *Tetrahedron Letters*, 38(30):5253-5256 (1997).

Vedejs, E., et al., "Heteroarene-2-sulfonyl Chlorides (BtsCl; ThsCl): Reagents for Nitrogen Protection and >99% Racemization-Free Phenylglycine Activation with $SOCl_2$," *J. Am. Chem. Soc.*, 118:9796-9797 (1996).

Corey, E. J., et al., "A Rational Approach to Catalytic Enantioselective Enolate Alkylation Using a Structurally Rigidified and Defined Chiral Quaternary Ammonium Salt under Phase Transfer Conditions," *J. Am. Chem. Soc.*, 119:12414-12415 (1997).

Bergeron, R., et al., "Desazadesmethyldesferrithiocin Analogues as Orally Effective Iron Chelators," *J. Med. Chem.*, 42:95-108 (1999).

Bergeron, R. et al., "The Desferrithiocin Pharmacophore," *J. Med. Chem.*, 37:1411-1417 (1994).

Bergeron, R. et al., "Effects of C-4 Stereochemistry and C-4 Hydroxylation on the Iron Clearing Efficiency and Toxicity of Desferrithiocin Analogues," *J. Med. Chem.*, 42:2432-2440 (1999).

Bergeron, R. et al., "Synthesis and Biological Evaluation of Naphthyldesferrithiocin Iron Chelators," *J. Med. Chem.*, 39:1575-1581 (1996).

Bergeron, R. et al., "Evaluation of Desferrithiocin and Its Synthetic Analogues as Orally Effective Iron Chelators," *J. Med. Chem.*, 34:2072-2078 (1991).

Bergeron, R. et al., "Evaluation of the Desferrithiocin Pharmacophore as a Vector for Hydroxamates," *J. Med. Chem.*, 42:2881-2886 (1999).

Bergeron, R. et al., "An Investigation of Desferrithiocin Metabolism," *J. Med. Chem.*, 37:2889-2895 (1994).

Bergeron, R. et al., "A Comparative Study of the Iron-Clearing Properties of Desferrithiocin Analogues with Desferrioxamine B in a *Cebus* Monkey Model," *Blood*, 81(8):2166-2173 (1993).

Bergeron, R., et al., "Pharmacokinetics of Orally Administered Desferrithiocin Analogs in *Cebus Apella* Primates," *Drug Metabolism and Disposition*, 27(12):1496-1498 (1999).

Mulqueen, G. C., et al., "Synthesis of the Thiazoline-based Siderophore (S)-Desferrithiocin," *Tetrahedron*, 49(24): 5359-5364 (1993).

O'Donnell, M. J., et al., "α-Methyl Amino Acids by Catalytic Phase-Transfer Aklylations," *Tetrahedron Letters*, 23(41):4259-4262 (1982).

Ehrler, Juerg, and Farooq, Saleem, "Total Synthesis of Thiangazole," *Synlett*, 702-704 (1994).

Kishore, V., et al., "Synthesis of α-Poly-[N$^\epsilon$-(2-aryl-Δ$^2$-thiazoline-4-carbonyl)$_L$-lysines] With Antiviral Activity," *Indian Journal of Chemistry* 15B: 255-257 (1977).

Zamri, Adel, and Abdallah, Mohamed A., "An Improved Stereocontrolled Synthesis of Pyochelin Siderophore of *Pseudomonas aeruginosa* and *Burkholderia cepacia*," *Tetrahedron* 56: 249-256 (2000).

Singh, Satendra, et al., "Efficient Asymmetric Synthesis of (*S*)- and (*R*) -*N*-Fmoc-*S*-Trityl-α-methylcysteine Using Camphorsultam as a Chiral Auxiliary," *J. Org. Chem.* 2004, pp. 4551-4554.

Shao, Hui, et al., "A New Asymmetric Synthesis of α-Methylcysteines via Chiral Aziridines," *J. Org. Chem.*, 1995, pp. 790-791.

Jeanguenat, A., et al., "Stereoselective Chain Elongation at C-3 of Cysteine Through 2,3-Dihydro-thiazoles, Without Racemization. Preparation of 2-Amino-5-hydroxy-3-mercaptoalkanoic Acid Derivatives," *J. Chem. Soc. Perkin Trans.* 1, 1991, pp. 2291-2298.

\* cited by examiner

SYNTHESIS OF 2-ALKYL AMINO ACIDS

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, pharmaceutically active peptidomimetic agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)- and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

The present invention includes a method of preparing a compound represented by Structural Formula (I):

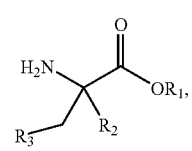

or a salt thereof; wherein:

$R_1$ and $R_2$ are, independently, —H or a substituted or unsubstituted alkyl group;

$R_3$ is —H, —$(CH_2)_xS(CH_2)_yH$, —$(CH_2)_xO(CH_2)_yH$, —$(CH_2)_xNH(CH_2)_yH$, —COOH, —$CONH_2$, —$NHC(NH)NH_2$, a substituted or unsubstituted alkyl group, a substituted or unsubstituted cycloaliphatic group, a substituted or unsubstituted heterocyclic group, a substituted or unsubstituted aromatic group, or a substituted or unsubstituted heteroaromatic group, wherein $R_3$ optionally comprises a protecting group;

x is an integer from 0–12; and y is an integer from 0–4;

comprising the steps of:

a.) reacting the compound represented by Structural Formula (III):

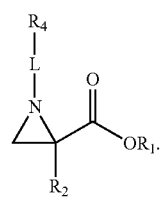

wherein:

L is a bond, a sulfoxide (—S(O)—), or a sulfone (—S(O)(O)—);

$R_4$ is a substituted or unsubstituted alkyl group or a substituted or unsubstituted aryl group; and $R_1$ and $R_2$ are as defined above;

with a nucleophile of the formula A-$R_3$, wherein A is —H, —Li, —MgCl, —MgBr, or —MgI, provided that A and $R_3$ are not each —H; and $R_3$ is as defined above; thereby forming a compound represented by Structural Formula (IV):

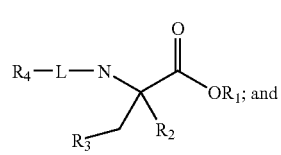

b.) cleaving L-$R_4$ and optionally the protecting group of $R_3$ from the compound represented by Structural Formula (IV), thereby forming the compound represented by Structural Formula (I).

In a first preferred embodiment, the aziridine represented by Structural Formula (III) is prepared by aziridinating a compound represented by Structural Formula (II):

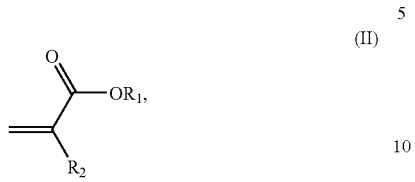

(II)

by reacting said compound with a source of nitrogen and an aziridination catalyst, thereby forming a compound represented by Structural Formula (III):

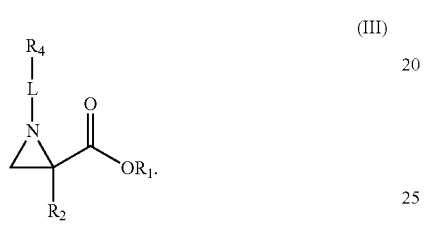

(III)

In a second preferred embodiment, the compound represented by Structural Formula (III) is prepared by reacting an epoxide represented by Structural Formula (IIa):

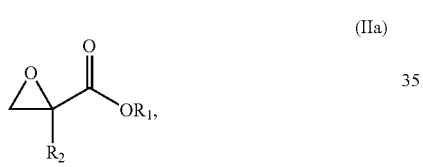

(IIa)

wherein $R_1$ and $R_2$ are as defined above, with a nucleophilic nitrogen compound, followed by a hydroxyl activating agent and a base. Functional groups, other than the epoxide moiety, which can react with the nucleophilic nitrogen compound, the hydroxyl activating agent and/or the base are preferably protected. Typically, this reaction occurs stereospecifically.

Either of these methods of preparing aziridines are suitable for use in the additional embodiments involving an aziridine intermediate. Methods specifically including aziridination of an alkene can have the alternative first step of converting an epoxide moiety into an aziridine moiety.

In one embodiment, the present invention is a method of preparing a compound represented by Structural Formula (VI):

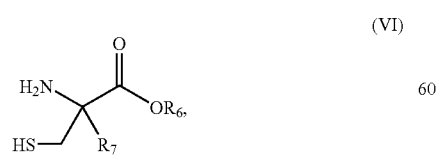

(VI)

or a salt thereof; where $R_6$ and $R_7$ are, independently, —H or a substituted or unsubstituted alkyl group; comprising the steps of:

a.) aziridinating a compound represented by Structural Formula (VII):

(VII)

by reacting said compound with a source of nitrogen and an aziridination catalyst, thereby forming a compound represented by Structural Formula (VIII):

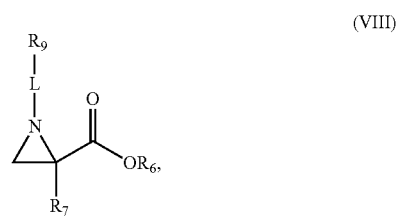

(VIII)

wherein L is a bond, sulfoxide (—S(O)—), or sulfone (—S(O)(O)—); $R_9$ is a substituted or unsubstituted alkyl group or a substituted or unsubstituted aryl group; and $R_6$ and $R_7$ are as defined above;

b.) reacting the compound represented by Structural Formula (VIII) with a nucleophile, A-S-Z, wherein A is —H; and Z is —H or a protecting group; thereby forming a compound represented by Structural Formula (IX):

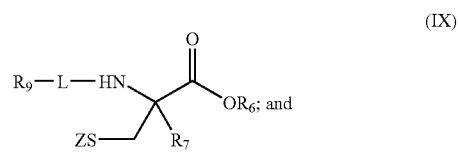

(IX)

c.) cleaving Z and L-$R_9$ from the compound represented by Structural Formula (IX), thereby forming the compound represented by Structural Formula (VI).

In another embodiment, the present invention is a method of preparing a compound represented by Structural Formula (XI):

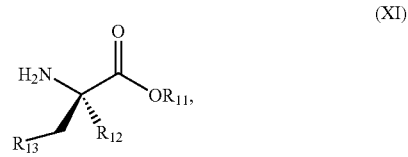

(XI)

or a salt thereof; where:

$R_{11}$ and $R_{12}$ are, independently, —H or a substituted or unsubstituted alkyl group;

$R_{13}$ is —H, —$(CH_2)_x$SH, —$(CH_2)_x$OH, —$(CH_2)_x$NH_2, —COOH, —$CONH_2$, a substituted or unsubstituted alkyl group, a substituted or unsubstituted aromatic group, or a substituted or unsubstituted heteroaromatic group; and x is an integer from 0–12;

comprising the steps of:

a.) aziridinating a compound represented by Structural Formula (XII):

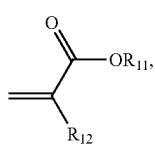

(XII)

by reacting said compound with a source of nitrogen and a stereospecific aziridination catalyst, thereby forming a compound represented by Structural Formula (XIII):

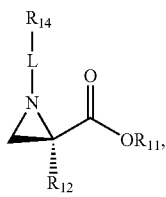

(XIII)

where L is a bond, sulfoxide (—S(O)—), or sulfone (—S(O)(O)—); $R_{14}$ is a substituted or unsubstituted alkyl group or a substituted or unsubstituted aryl group; and $R_{11}$ and $R_{12}$ are as defined above;

b.) reacting the compound represented by Structural Formula (XIII) with a nucleophile, A-$R_{13}$, where A is —H, —Li, —MgCl, —MgBr, or —MgI, provided that A and $R_{13}$ are not each —H; and $R_{13}$ is as defined above; thereby forming a compound represented by Structural Formula (XIV):

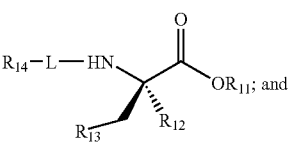

(XIV)

c.) cleaving L-$R_{14}$ and optionally the protecting group of $R_{13}$ from the compound represented by Structural Formula (XIV), thereby forming the compound represented by Structural Formula (XI).

The above methods preferably comprise the additional step of resolving enantiomers or diasteromers of a 2-alkyl amino acid (or an ester or a salt thereof). Synthetic methods leading to a substantial excess of an enantiomer or diastereomer (e.g., asymmetric syntheses producing >85% ee, >90% ee, or >95% ee) can be purified or ultrapurified by an additional resolution step. More preferably, methods of the present invention comprise isolating the (R)- and (S)-enantiomers of 2-alkyl amino acids, or esters or salts thereof.

The present invention also includes a method of preparing a compound represented by Structural Formula (XVI):

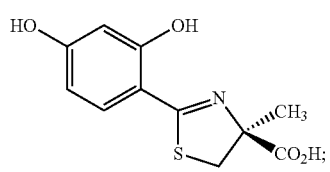

(XVI)

comprising the step of coupling (S)-2-methylcysteine or a salt thereof, as prepared by a method described above, to 2,4-dihydroxybenzonitrile. Alternatively, an analogous compound can be synthesized by coupling 2-hydroxybenzonitrile and (S)-2-methylcysteine or a salt or an ester thereof. Similar syntheses can be conducted with other substituted benzonitriles.

Advantages of the present invention include the facile synthesis of a 2-alkyl amino acid from an alkylacrylate. Additional advantages include the ability to prepare amino acids with a wide variety of side chains, such as preparing 2-methylcysteine. 2-Methylcysteine prepared by the method of the present invention can be coupled to 2,4-dihydroxybenzonitrile to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing 2-alkyl amino acids involves the aziridination of alkylacrylates. The aziridinated alkylacrylate can be further reacted to form 2-alkyl amino acids having a wide variety of side chains.

Aziridinations of the present invention typically include reacting an alkylacrylate with a source of nitrogen. Aziridinations are typically conducted under a nitrogen or other inert atmosphere, often at ambient pressure. Suitable solvents for an aziridination include acetonitrile; acetonitrile in 5–15% water, methanol, ethanol, or t-butanol; dimethylformamide (DMF); dimethylformamide (DMSO); tetrahydrofuran (THF); and acetonitrile in 5–25% DMF, DMSO, or THF. Reaction temperatures are typically about 0° C. to about 100° C., about 20° C. to about 80° C., about 25° C. to about 60° C., or about 30° C. to about 50° C. Aziridinations are further described in U.S. Pat. Nos. 5,929,252 and 5,789,599, which are incorporated herein by reference. Aziridinations can be conducted in a continuous process, such that no intermediate purifications are required, although such purifications are optional.

Preferred sources of nitrogen include compounds represented by the Structural Formulas (V), (X), and (XV):

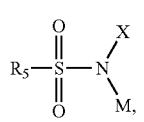

(V)

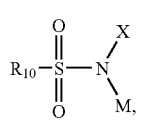

(X)

-continued

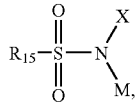
(XV)

where M is an alkali metal, X is a halide, and $R_5$, $R_{10}$, and $R_{15}$ are each a substituted or unsubstituted alkyl group or substituted or unsubstituted aryl group. Preferably, M is sodium and X is chloride or bromide. Preferred $R_5$, $R_{10}$, and $R_{15}$ groups include phenyl, tolyl, p-nitrophenyl, n-butyl, t-butyl, and methyl. An especially preferred $R_5$, $R_{10}$, and $R_{15}$ is p-tolyl.

Preferred aziridination catalysts include transition metal halides, alkaline earth metal halides, $Rh_2(acetate)_4$, a dihalogen, phenyltrimethlammonium tribromide, and pyridinium hydrobromide. Copper halides are especially preferred aziridination catalysts.

Preferred stereospecific aziridination catalysts include copper 4,4'-disubstituted bis(oxazolines). Examples of 4,4'-disubstituted bis(oxazolines) are represented by the structural formula:

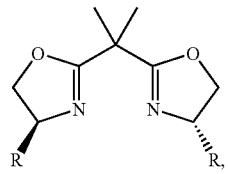

where R is an alkyl or an arylalkyl group. Preferably, R is —$CH(CH_3)_2$, —$C_6H_5$, —$C(CH_3)_3$, —$C(CH_3)_2(C_6H_5)$, or —$C(CH_3)(C_6H_5)_2$. Copper 4,4'-disubstituted bis(oxazolines) can be formed, for example, by reacting a copper(I) or copper(II) salt with a 4,4'-disubstituted bis(oxazoline). Acceptable copper(I) and copper(II) salts include copper(I) triflate, copper(II) triflate, copper(I) chloride, and copper(I) bromide. Stereospecific aziridination catalysts are further described in Evans, et al., *J. Am. Chem. Soc.* 116: 2742–2753 (1994); Evans, et al., *J. Am. Chem. Soc.,* 115: 5328–5329 (1993); and Johnson et al., *Acc. Chem. Res,.* 33: 325–335 (2000); which are incorporated herein by reference.

Additional stereospecific aziridination catalysts include zeolites. Suitable zeolites typically comprise a transitional metal such as copper in copper-exchanged zeolites (e.g., copper-exchanged zeolite Y, obtained from Union Carbide as ultrastabilized $NH_4^+Y$ zeolite) described in publications by Langham et al., Applied Catalysis A 182: 85–89 (1999); Langham et al., J. Chem. Soc., Perkin Trans. 2: 1043–1049 (1999); and Langham et al., J. Chem. Soc. Chem. Commun. 1601–1602 (1998); Gullick, et al., J. Mol. Catalysis A—Chem. 180: 85–89 (2002); Gullick, et al., Catalysis Lett., 75: 151–154 (2001); and Taylor, et al., J. Chem. Soc. Perkins Trans. 2: 1714–1723 (2001); the entire contents of which are incorporated herein by reference.

Reaction of an aziridine with a nucleophile is conducted in an appropriate solvent and at appropriate temperature. Typically, the solvent is an aprotic solvent such as acetonitrile, dimethylformamide, dioxane, ethyl acetate, ethyl ether, hexamethylphosphoramide, and tetrahydrofuran. Appropriate temperatures are typically about 0° C. to about 90° C., about 20° C. to about 70° C., or about 30° C. to about 60° C.

Acceptable nucleophiles typically have the formula A-$R_3$, where A is —H, —Li, —MgCl, —MgBr, or —MgI; and $R_3$ is as defined above. Nucleophiles typically have a heteroatom such as N, O, or S, or a metal-carbon bond such as Li—C or Mg—C. Nucleophiles can have a protecting group. Preferably, $R_3$ is —SH or a protected variant thereof. More preferably, A-$R_3$ is $CH_3COSH$ or $C_6H_5C(O)SH$.

A second type of aziridination involves the opening of an epoxide ring with a nucleophilic nitrogen compound. Nucleophilic nitrogen compounds are advantageously generated in situ, whereby the compounds typically have a protecting group that is removed under reaction conditions. Protecting groups typically include those disclosed herein as being suitable for protecting nitrogen atoms (e.g., Boc). Examples of suitable nucleophilic nitrogen compounds include secondary and tertiary, preferably secondary, nitrogen atoms bonded to one or two protecting groups and a second substituent that is preferably not removed under the same conditions as the protecting group (e.g., a substituted phenyl sulfonyl group such as nosyl, tosyl or brosyl).

The ring-opened product (an alpha, beta-aminoalcohol) is subsequently reacted with a hydroxyl activating agent and an anhydrous base (e.g., pyridine, dimethylaminopyridine, dimethylmorpholine, another amine disclosed herein or combination thereof) in an appropriate solvent in order to form an aziridine. The hydroxyl activating agent converts the hydroxyl group into a better leaving group, such that it can be displaced by the amino moiety. Examples of hydroxyl activating agents include triphenylphosphine and alkyl or aryl sulfonates such as methane sulfonic anhydride, methane sulfonic chloride, toluene sulfonic chloride and trifluoroacetic chloride. A substituted phenyl sulfonyl group can be removed upon formation of the aziridine ring, or a time later in the synthesis. Cleavage of a substituted phenyl sulfonyl group is essentially identical to the cleavage of L-$R_4$ and the like from an aziridine, as described below.

Examples of the conversion of epoxides to aziridines can be found, for example, in the following: U.S. Pat. No. 5,929,232; PCT Publication No. WO00/01670; Fuji, K., Kawabata, T., Kiryu, Y., Sugiura, Y., Taga, T., Miwa, Y., "A New Access to Chiral Aziridines by Enzymatic Transesterification of meso-Bis(acetoxymethyl)aziridines," *Tetrahedron Lett.* 31, 6663–6666 (1990); Ittah, Y., Sasson, Y., Shahak, I., Tsaroom, S., Blum, J., "A New Aziridine Synthesis from 2-Azido Alcohols and Tertiary Phosphines. Preparation of Phenanthrene 9,10-Imine," *J. Org. Chem.,* 43, 4271–4273 (1978); Konsler, R. G., Karl, J., Jacobsen, E. N., "Cooperative Asymmetric Catalysis Using Dimeric Salen Complexes," *J. Am. Chem. Soc.,* 120, 10780–10781 (1998); Larrow, J. F., Roberts, E., Verhoeven, T. R., Ryan, K. M., Senanayake, C. H., Reider, P. J., Jacobsen, E. N., "(1S,2R)-1-Aminoindan-2-ol," *Organic Synth.* 76, 46–56 (1998), Annis, D. A., Jacobsen, E. N., "Polymer-Supported Chiral Co(Salen) Complexes: Synthetic Applications and Mechanistic Investigations in the Hydrolytic Kinetic Resolution of Terminal Epoxides," *J. Am. Chem. Soc.,* 121, 4147–4154 (1999); Senanayake, C. H., Jacobsen, E. N., "Chiral (Salen) Mn(III) Complexes in Asymmetric Epoxidations: Practical Synthesis of cis-Aminoindanol and Its Application to Enantiopure Drug Synthesis," in Process Chemistry in the Pharmaceutical Industry, Gadamasetti, K. G., Ed., Dekker: New York, 1999, pp. 347–368; Myers, J. K., Jacobsen, E. N., "Asymmetric Synthesis of Amino Acid Derivatives via Catalytic Conjugate Addition of Hydrazoic Acid to Unsaturated Imides," *J. Am. Chem. Soc.* 121, 8959–8960 (1999); Jacobsen, E. N., Wu, M. H., "Ring Opening of Epoxides and Related Reactions," in Comprehensive Asymmetric Catalysis, Jacobsen, E. N., Pfaltz, A., Yamamoto, H., Eds., Springer: New York, 1999, Chapter 35; Jacobsen, E. N., "Aziridination," in Comprehensive Asymmetric Catalysis, Jacobsen, E. N., Pfaltz, A., Yamamoto, H., Eds., Springer: New York, 1999, Chapter 17; Jacobsen, E. N., "Future Perspectives in Asymmetric Catalysis," in Comprehensive Asymmetric Catalysis, Jacobsen, E. N., Pfaltz, A., Yamamoto, H., Eds., Springer: New York, 1999, Chapter 42; Li, Z., Fernandez, M., Jacobsen, E. N., "Enantioselective Ringopening of meso Aziridines Catalyzed by Tridentate Schiffbase Chromium(III) Complexes," *Org. Lett.* 1, 1611–1613 (1999); Schaus, S. E., Jacobsen, E. N., "Asymmetric Ring-Opening of Meso-Epoxides with TMSCN Catalyzed by (pybox)Lanthanide Complexes," *Org. Lett.* 2, 1001–1004 (2000); Brandes, B. D., Jacobsen, E. N., "Regioselective Ring Opening of Enantiomerically Enriched Epoxides via Catalysis with Chiral (Salen)Cr(III) Complexes," *Synlett* 1013–1015 (2001); M. K. Gurjar, K. Sadalapure, S. Adhikari, B. V. N. B. S. Sarma and M. S. Chorghade, "Kinetic Resolution of Aryl Glycidyl Ethers: A Practical Synthesis of Optically Pure beta-blocker-S-Metoprolol", *Heterocycles* 48 (7), 1471 (1998); Mukund K. Guijar, L. Murali Krishna, Bugga V. N. B. S. Sarma and Mukund S. Chorghade, "A Practical Synthesis of (R)-(–)-Phenylephrine Hydrochloride", *Org. Process Res. Dev.,* 2(6), 422 (1998); M. S. Chorghade, M. K. Gurjar, S. Adhikari, K. Sadalapure, S. V. S. Lalitha, A. M. S. Murugaiah and P. Radha Krishna, "Synthesis of (2S,5S)-trans-5-(4-fluorophenoxymethyl)-2-(1-N-hydroxyureidyl-3-butyn-4-yl)-tetrahydrofuran-CMI-977", *Pure and Appl. Chem.* 1071–74 (1999); Ramesh A. Joshi, Mukund K. Gurjar, Narendra K. Tripathy and Mukund S. Chorghade, "A New and Improved Process for Celiprolol Hydrochloride", *Organic Process Research and Development* 5(2), 176 (2001); and Mukund K. Gurjar, A. M. S. Murugaiah, P. Radhakrishna, C. V. Ramana and Mukund S. Chorghade, "A Novel and Simple Asymmetric Synthesis of CMI-977 (LDP-977): A potent Anti-Asthmatic Drug Lead", *Tetrahedron Asymmetry*, In Press, 2003; the contents of each of which are incorporated herein by reference.

Cleavage of $L-R_4$, $L-R_9$ or $L-R_{14}$ can be achieved by, for example, hydrolysis with bases such as potassium hydroxide, sodium hydroxide or methoxides (e.g., sodium methoxide, potassium methoxide); reduction; reaction with compounds such as tetrabutylammonium fluoride and basic thiophenol. Cleavage reactions are further described in Yasuhara, et al., *Tetrahedron Lett.* 39: 595–596 (1998); Maligres, et al., *Tetrahedron Lett.* 38: 5253–5256 (1997); and Vedejs, et al., *J. Am. Chem. Soc.* 118: 9796–9797 (1996); each of which is incorporated herein by reference.

Cleavage of a protecting group is dependent on the nature of the protecting group. For example, an acyl protecting group can be removed by treating the protecting group with acids such as hydrochloric acid, acetic acid, dilute sulfuric acid, and the like; and bases such as sodium hydroxide, potassium hydroxide, sodium methoxide, potassium methoxide, sodium ethoxide, potassium ethoxide, and ammonia. Other examples of removing protecting groups can be found in "Protective Groups in Organic Synthesis, 3$^{rd}$ Edition" by Peter G. M. Wuts and Theodora W. Greene, Wiley-Interscience, 1999, which is incorporated herein by reference. Protecting group cleavage (e.g., of the carboxylic acid and/or the amino acid sidechain) can occur simultaneously with cleavage of $L-R_4$, $L-R_9$ or $L-R_{14}$.

If not prepared by an asymmetric synthesis, 2-alkyl amino acids and functionalized derivatives prepared by the above-described methods are preferably resolved. 2-Alkyl amino acids and derivatives thereof prepared by asymmetric synthetic methods can be ultrapurified by further resolution. Typically, amino acids are resolved by forming a diastereomeric salt with an amino acid and a chiral amine. Suitable chiral amines include arylalkylamines such as (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Resolution of chiral compounds using diastereomeric salts is further described in *CRC Handbook of Optical Resolutions via Diastereomeric Salt Formation* by David Kozma (CRC Press, 2001), which is incorporated herein by reference in its entirety.

Alternatively, 2-alkyl amino acids and functionalized derivatives (e.g., esters) can be resolved by emulsion crystallization, as described in U.S. Pat. Nos. 5,872,259, 6,383,233 and 6,428,583, which are incorporated herein by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication typically helps the process of forming an emulsion. The mixture is then seeded with crystals of the desired, optically active acid along with an additional quantity of surfactant and an anti-foaming agent. The desired product usually crystallizes out and can be separated by filtration. Further details of emulsion crystallization for an amino acid derivative can be found in Example 4.

Once the 2-alkyl amino acids have been resolved, the desired isomer can be isolated. Typically, a (S)-2-amino acid or an ester thereof is isolated. Preferably, (S)-2-methylcysteine or (S)-2-methylcysteine methyl ester is isolated.

Cysteine, a 2-alkylcysteine such as (S)-2-methylcysteine, or a cysteine alkyl ester can be coupled to a substituted or unsubstituted aryl nitrile such as a substituted or unsubstituted benzonitrile. Preferably, the substituents on benzonitrile will not interfere with the coupling reaction. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Typically, coupling of cysteine, a 2-alkylcysteine, or a cysteine alkyl ester and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. Alternatively, cysteine or a related compound can be coupled directly with a benzimidate. The benzimidate is then reacted with the cysteine (or related compound) under basic conditions. Acceptable bases include trimethylamine, triethylamine, triphenylamine, dimethylamine, diethylamine, diphenylamine, diisopropylamine, other dialkylamines, diisopropylethylamine, 1,4-diazabicyclo[2.2.2]octane (DABCO), 1,5-diazabicyclo[4.3.0]non-5-ene (DBN), $CaCO_3$, $Cs_2CO_3$, sodium hexamethyl disilazide, potassium hexamethyl disilazide, and other alkali and alkaline earth metal salts. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080 to Raymond J. Bergeron, Jr., the contents of which are incorporated herein by reference. Additional examples can be found in PCT/US93/10936, PCT/US97/04666, and PCT/US99/19691, the contents of which are incorporated by reference.

Suitable benzonitriles and benzimidates for use in the above coupling reaction can be synthesized by methods described in U.S. application Ser. Nos. 60/381,013, 60/380,878 and 60/380,909, all filed May 15, 2002; the entire teachings of which are incorporated herein by reference.

$R_1$, $R_2$, $R_6$, $R_{11}$, and $R_{12}$ are preferably unsubstituted alkyl groups. Preferably, $R_1$, $R_2$, $R_6$, $R_{11}$, and $R_{12}$ are each methyl. $R_7$ is preferably methyl or benzyl, where the methyl or benzyl group can be substituted or unsubstituted.

$R_3$ and $R_{13}$ include —H, —$(CH_2)_xS(CH_2)_yH$, —$(CH_2)_xO(CH_2)_yH$, —$(CH_2)_xNH(CH_2)_yH$, —$(CH_2)_xC(O)NH_2$, —$(CH_2)_xC(O)OH$, —$(CH_2)_xNHC(NH)NH_2$, a C1–C6 substituted or unsubstituted alkyl group,

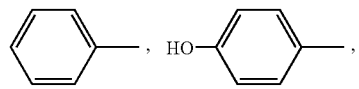

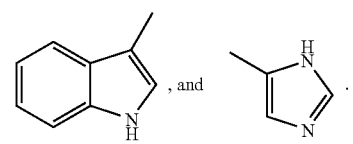

Additional suitable examples of $R_3$ include —$CONH_2$, —$CH_2CONH_2$, —$CH_2CH_2CONH_2$, —$CH_2CH_2CH_2CONH_2$, —SH, —$CH_2SH$, —$CH_2CH_2SH$, —$CH_2CH_2CH_2SH$, —$CH(CH_3)_2$, —$CH_2CH(CH_3)_2$, —$CH_2CH_2CH(CH_3)_2$, —$CH_2CH_2CH_2CH(CH_3)_2$, —$SCH_3$, —$CH_2SCH_3$, —$CH_2CH_2SCH_3$, —$CH_2CH_2CH_2SCH_3$, —OH, —$CH_2OH$, —$CH_2CH_2OH$, —$CH_2CH_2CH_2OH$, —COOH, —$CH_2COOH$, —$CH_2CH_2COOH$, —$CH_2CH_2CH_2COOH$, —$NHC(NH)NH_2$, —$CH_2NHC(NH)NH_2$, —$CH_2CH_2NHC(NH)NH_2$, —$CH_2CH_2CH_2NHC(NH)NH_2$, —$NH_2$, —$CH_2NH_2$, —$CH_2CH_2NH_2$, —$CH_2CH_2CH_2NH_2$,

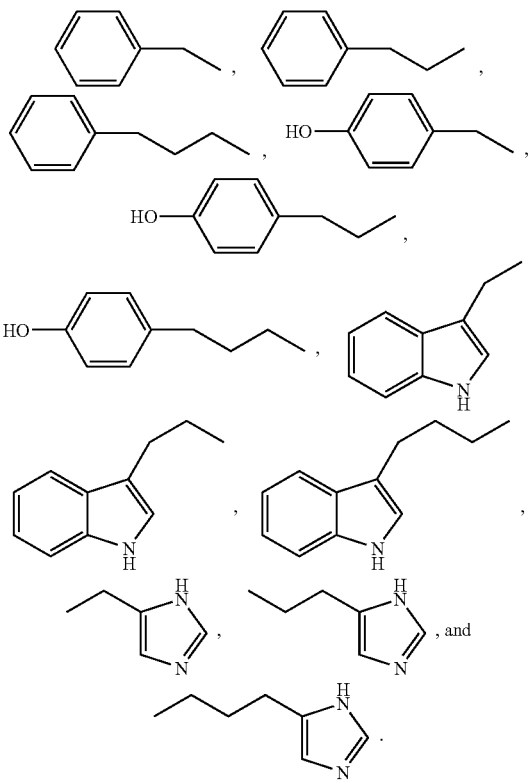

Preferred values of x include integers from 0–12, 0–6, 0–4, 0–3, 0–2, and 0–1. Zero is an especially preferred value of x.

Preferred values of y include integers from 0–4, 0–3, 0–2, and 0–1. Zero and one are especially preferable values of y.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

A cycloaliphatic group is cyclic, non-aromatic, consists solely of carbon and hydrogen and may optionally contain one or more units of unsaturation, e.g., double and/or triple bonds. A cycloaliphatic group can have one or more rings, which can be fused together. Typically, a cycloaliphatic group has one to about 24 carbons atoms, or about 1 to about 12 carbon atoms. Examples of cycloaliphatic groups include cyclopentyl, cyclohexyl, cycloheptyl, cyclooctyl, cyclodecyl, cyclopentenyl, cyclopenta-1,3-dienyl, cyclohexenyl, cyclohexa-1,3-dienyl, cyclohexa-1,4-dienyl, cycloheptenyl, cyclooctenyl, cycloocta-1,3-dienyl, and cycloocta-1,3,5-trienyl.

A heterocyclic group is a cycloaliphatic group where one or more of the carbon atoms are replaced by a heteroatom such as S, O, or N. Examples of heterocyclic groups include oxiryl, oxetyl, oxolyl, oxyl, aziridyl, azetidyl, pyrrolidyl, piperidyl, tetrahydrothiophyl, and tetrahydrothiopyryl.

Aromatic (or aryl) groups include carbocyclic aromatic groups such as phenyl, p-tolyl, 1-naphthyl, 2-naphthyl, 1-anthracyl and 2-anthracyl. Heteroaromatic groups include N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl and cycloaliphatic groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aromatic group. Alkyl and cycloaliphatic groups can additionally be substituted by a heterocyclic, aromatic, or heteroaromatic group (e.g. an alkyl group can be substituted with an aromatic group to form an arylalkyl group). A substituted alkyl or cycloaliphatic group can have more than one substituent.

Suitable substituents for heterocyclic, aromatic, and heteroaromatic groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aromatic group. Heterocyclic, aromatic, and heteroaromatic groups can additionally be substituted by an alkyl or cycloaliphatic group (e.g. an aryl group can be substituted with an alkyl group to form an alkylaryl group such as tolyl). A substituted heterocyclic, aromatic, or heteroaromatic group can have more than one substituent.

Functional groups of the present invention can be protected with a protecting group. As is known in the art, a protecting group reduces or eliminates the ability of a functional group to react with another functional group. For example, a thiol or an alcohol can be protected with an acyl group. Similarly, an alcohol can be protected by a tosyl or a trimethylsilyl group. An amine can, for example, be protected by an Fmoc group or a Boc group. Additional protecting groups, methods of adding a protecting group, and methods of removing a protecting group are taught in "Protective Groups in Organic Synthesis, 3$^{rd}$ Edition" by Peter G. M. Wuts and Theodora W. Greene, Wiley-Interscience, 1999, which was incorporated by reference above.

Protecting groups for basic nitrogen atoms include formyl; 4-toluenesulfonyl; t-butyloxycarbonyl; 2,4-dinitrophenol; benzyloxymethyl; trityl; t-butoxymethyl; 2-chlorobenzyloxy-carbonyl; allyloxycarbonyl; benzyloxycarbonyl (Z); mesitylene-2-sulfonyl; 4-methyloxy-2,3,6-trimethyl-benzyenesulfonyl; 2,2,5,7,8-pentamethylchroman-6-sulfonyl; 9-xanthenyl; and 2,4,6-trimethoxybenzyl.

Protecting groups for basic sulfur groups include 4-methylbenzyl, 3-nitro-2-pyridinesulfenyl; trityl; 2,4,6-trimethoxybenzyl; acetamidomethyl; trimethylacetaminomethyl; t-butylsulfonyl; and sulfoxide.

Protecting groups for basic oxide groups include benzyl ether; t-butyl ether; benzyl ether; 2,6-dichlorobenzyl ether; 2-bromobenzyl ether; and 3,5-dibromobenzyl ether.

Carboxyl groups can be protected, for example, as ethers or as carboxamides. For example, when a carboxyl group is protected as an ether, it takes the form of —COOR wherein R is a substituted or unsubstituted C1 to C10 alkyl group, a substituted or unsubstituted up to C30 alkyl group, or a substituted or unsubstituted alkyl-aryl group wherein the alkyl group is C1 to C5 and the aryl group is up to C30. When a carboxyl group is protected as a carboxamide, it takes the form of —CONR' wherein R' is —H or as in R above.

Also included in the present invention are salts of the disclosed amino acids and amino acid esters (including side chains). For example, amino acids can also be present in the anionic, or conjugate base, form, in combination with a cation. Suitable cations include alkali metal ions, such as sodium and potassium ions, alkaline earth ions, such as calcium and magnesium ions, and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

Sources of nitrogen also include sulfinimines such as N-benzylidene-p-toluenesulfinimine, 4-methoxybenzylidene-p-toluenesufinimine, N-isobutylidene-p-toluenesulfinimine, N-(3-phenyl-(E)-2-propylidene)-p-toluenesulfinimine, and N-(2-methyl-(E)-2-butenylidene)-p-toluenesulfinimine; (N-p-tolylsulfonyl)imino) phenyliodinane); and tosyl azide.

EXAMPLE 1

Synthesis of
N-p-Toluenesulfonyl-2-carbomethoxy-2-methyl aziridine

Bromamine-T (3 g, 11.028 mmol) was added to a stirred mixture of anhydrous CuCl$_2$ (148 mg, 1.1 mmol) and methyl methacrylate (5.14 g, 5.88 mL, 5.5 mmol) in acetonitrile (30 mL) at room temperature under nitrogen. The reaction mixture was stirred at room temperature overnight. Then it was diluted with ethyl acetate (100 mL) and filtered through a pad of silica gel. The filtrate was dried over sodium sulfate and the solvent was concentrated in vacuo. A thick colorless oil obtained was purified through silica gel column chromatography with an eluent mixture of petroleum ether:ethyl acetate (1:4) to yield 2.1 g (70%) of the pure aziridine product. The product was characterized by $^1$H NMR (200 MHz), mass spectrometry, and FT-IR spectral analysis.

Synthesis of methyl
(2-N-tosylamino-3-benzoylmercapto) propionate

Thiobenzoic acid (253 mg, 1.85 mmol) was added to a stirred solution of N-p-Toluenesulfonyl-2-carbomethoxy-2-methyl aziridine (250 mg, 0.929 mmol) in anhydrous dichloromethane (5 mL). The reaction mixture was stirred at room temperature for 18 h and at 40° C. for 30 h. It was then diluted with ethyl acetate (40 mL) and the combined organic layer was washed with saturated sodium bicarbonate solution and dried. Removal of the solvent under vacuum yielded an oily residue, which crystallized upon the addition of hexane to yield 150 mg (39%) of the pure product. The product was characterized by $^1$H NMR, FT-IR and mass spectrometry.

Synthesis of methyl (2-N-tosylamino-3-mercapto) propionate

Methyl N-tosyl amino-3-benzoyl mercapto propionate was dissolved in 30 mL of 0.2 N NaOH. The solution was kept under nitrogen at room temperature for 15 minutes. The reaction mixture was acidified with dilute sulfuric acid and the solution was extracted with ethyl acetate. The ethyl acetate layer was washed with water until the water extract became neutral and was dried over sodium sulfate and concentrated to a small volume in vacuo. Analysis of the isolated products from the reaction mixture did not show any indication of both tosyl and methyl groups. The product isolated from the ethyl acetate layer contained a cleaved benzoyl compound.

EXAMPLE 2

Synthesis of N-p-Toluenesulfonyl-2-carbomethoxy-2-methyl aziridine

Bromamine-T (3 g, 11.028 mmol) was added to a stirred mixture of anhydrous $CuCl_2$ (148 mg, 1.1 mmol) and methyl methacrylate (5.14 g, 5.88 mL, 5.5 mmol) in acetonitrile (30 mL) at room temperature under nitrogen. The reaction mixture was then stirred at room temperature overnight, then diluted with ethyl acetate (100 mL) and filtered through a pad of silica gel. The filtrate was dried over sodium sulfate and the solvent was concentrated in vacuo. An oil was obtained and purified through silica gel column chromatography with an eluent mixture of petroleum ether:ethyl acetate (1:4) to yield 2.1 g (70%) of the pure aziridine product.

Synthesis of methyl (2-N-tosylamino-3-benzoylmercapto) propionate

Thiobenzoic acid (253 mg, 1.85 mmol) was added to a stirred solution of N-p-toluenesulfonyl-2-carbomethoxy-2-methyl aziridine (250 mg, 0.929 mmol) in anhydrous dichloromethane (5 mL). The reaction mixture was stirred at room temperature for 18 h and at 40° C. for 30 h. It was then diluted with ethyl acetate (40 mL) and the combined organic layer washed with saturated sodium bicarbonate solution and dried. Removal of the solvent under vacuum yielded an oily residue, which crystallized upon the addition of hexane to yield 150 mg (39%) of the pure product. The product was characterized by $^1$H NMR, FT-IR and Mass spectrometry.

Synthesis of methyl (2-N-tosylamino-3-mercapto) propionate

Methyl N-tosyl amino-3-benzoyl mercapto propionate is dissolved in an aqueous ammonia solution. The mixture is stirred for a time, then acidified. The solution is extracted with a suitable solvent, and the product is isolated.

EXAMPLE 3

Synthesis of N-p-toluenesulphonyl-2-carbomethyoxy-2-methyl aziridine

Anhydrous $CuCl_2$ (148 mg, 1.1 mmol) in acetonitrile (30 ml) was stirred under nitrogen at room temperature. Methyl methacrylate (1.1 g, 1.17 ml, 11 mmol) was then added to this solution followed by addition of Bromamine-T (1.793 g, 5 mmol). The reaction mixture was stirred at room temperature for 6–8 hours. Then it was diluted with ethyl acetate (100 ml) and filtered through a pad of silica gel. The clear solution was dried over sodium sulphate and solvent concentrated under vacuum. A thick colorless oil was obtained, which was purified by silica gel column chromatography (eluent of petroleum ether:ethyl acetate: 4:1) to obtain N-p-toluenesulfonyl-2-carbomethoxy-2-methyl aziridine. The reaction yielded 1.3 g (40%).

$^1$H NMR ($CDCl_3$) 200 MHz: δ 1.88 (s, 3H, $CH_3$), 2.42 (s, 3H, $CH_3$), 2.70 (s, 1H), 2.78 (s, 1H), 3.73 (s, 3H, $COOCH_3$), 7.30–7.33 (d, 2H, aromatic), 7.80–7.84 (d, 2H, aromatic).

Synthesis of methyl (2-N-tosylamino-3-benzoylmercapto)propionate

N-p-Toluenesulphonyl-2-carbomethoxy-2-methyl aziridine (250 mg, 0.229 mmol) was dissolved in 5 ml of $CH_2Cl_2$ and thiobenzoic acid (253 mg, 1.85 mmol) was added to this solution. The reaction mixture was stirred at room temperature for 18 hours and at 40° C. for 30 hours. It was then diluted with ethyl acetate (40 ml); the combined organic layer was washed with saturated sodium bicarbonate solution and dried. Removal of the solvent under vacuum yielded an oily residue, which crystallized upon the addition of hexane. The reaction yielded 150 mg methyl (2-N-tosylamino-3-benzoylmercapto)proionate (39%), which had a melting point of 137–138° C. Other analytical data are as follows:

IR ($CHCl_3$): 3279 $cm^{-1}$ (NH), 1733 $cm^{-1}$ (ester), 1667 $cm^{-1}$ (ketone).

$^1$H NMR ($CDCl_3$), 200 MHz: δ 1.54 (s, 3H, $CH_3$), 2.38 (s, 3H, $CH_3$), 3.48–3.55 (d, 2H, $CH_3$), 3.67 (s, 3H, $COOCH_3$), 5.67 (s, 1H, NH), 7.25 (d, 2H, aromatic), 7.40–7.77 (m, 5H, aromatic), 7.95 (d, 2H, aromatic).

Mass (m/e): 408 ($M^{+1}$), 348 (M–$COOCH_3$).

CH analysis Calculated for: $C_{19}H_{21}NO_5S_2$: C=56.0%; H=5.15%; N=3.43%; S=15.72% Found: C=56.56%; H=4.92%; N=3.12%; S=16.40%.

EXAMPLE 4

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20° C.).

45 mg of (R,R)- and (S,S)-amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)-(−) amino acid or its ester crystals grown under similar conditions. After 2 hours of agitation the resulting crystals were filtered off, washed with water and dried in a gentle nitrogen stream.

EXAMPLE 5

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 6

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

EXAMPLE 7

Synthesis of N-p-Toluenesulphonyl-2-carbomentoxy-2-methylaziridine

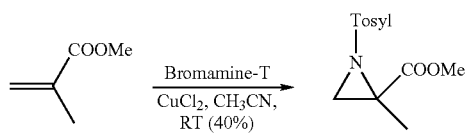

Anhydrous $CuCl_2$ (148 mg, 1.1 mmol) in acetonitrile (30 ml) was stirred under nitrogen at room temperature. Methyl methacrylate (1.1 g, 1.17 ml, 11 mmol) was then added to this solution, followed by addition of Bromamine-T (1.79 g, 5 mmol). The reaction mixture was stirred at room temperature for 6–8 hours. It was diluted with ethyl acetate (100 ml) and filtered through a pad of silica gel. The clear solution was dried over sodium sulphate and the solvent was concentrated under vacuum. A thick colorless oil was obtained, which was purified by silica gel column chromatography (eluent: petroleum ether:ethyl acetate 4:1). The reaction yielded 628.9 mg of product (40%).

Spectral Data

IR (Neat): 3020; 1741; 1331; 1215; 1163; 882; 759 cm$^{-1}$.
$^1$H NMR(CDCl$_3$), 200 MHz: δ 7.78 (d, J=8 Hz, 2H); 7.34 (d, J=8 Hz, 2H); 3.72 (s, 3H); 3.50 (m, J=15 Hz, 1H); 2.75 (d, J=15 Hz, 1H); 2.45 (s, 3H); 1.96 (s, 3H)

Mass (m/e): 269 (6); 238 (12); 210 (9); 184 (7); 155 (25); 114 (100); 91 (98); 77 (10); 65 (60).
$^{13}$C NMR(CDCl$_3$): δ 166.27; 143.75; 136.40; 129.16; 126.95; 52.26; 45.90; 38.22; 24.91; 20.87; 14.59.

CH analysis Calculated for $C_{12}H_{15}NO_4S$: C=53.53%; H=5.51%; N=5.20%, S=11.89% Found C=49.65%; H=5.81%; N=4.93%; S=12.52%

Synthesis of Methyl (2-N-tosylamino-3-benzoylmercapto)propionate

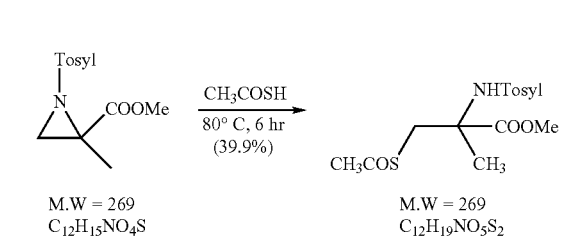

N-p-Toluenesulphonyl-2-carbomethoxy-2-methyl aziridine (200 mg, 0.743 mmol) was added to a 5 ml two necked round bottom flask under nitrogen, then thioacetic acid (0.816 ml, 11.14 mmol) was added. The reaction mixture was heated at 80° C. for 6 hours. It was then diluted with ethyl acetate (40 ml); the combined organic layer was washed with saturated sodium bicarbonate solution and dried. Removal of the solvent under vacuum yielded an oily residue, which was purified by column chromatography. The reaction yielded 51.30 mg of product (39.9%).

Spectral Data

IR (Neat): 3280; 1740; 1694; 1597; 1331; 1159 cm$^{-1}$.
$^1$H NMR(CDCl$_3$), 200 MHz: δ 7.72 (d, J=8Hz, 2H); 7.3 (d, J=8 Hz, 2H); 5.53 (s, 3H); 3.65 (s, 3H); 3.40 (q, 2H); 2.42 (2, 3H); 2.32 (s, 3H); 1.26 (s, 3H)

Mass (m/e): 286 (4); 256 (4); 155 (77); 139 (12); 114 (10); 9 (100); 77 (3); 65 (13).
$^{13}$C NMR(CDCl$_3$): δ 193.82; 171.54; 142.80; 138.50; 128.90; 126.40; 61.16; 52.45; 37.04; 29.69; 21.35; 20.83.

CH analysis Calculated for $C_{14}H_{19}NO_5S_2$: C=48.91%; H=5.51%;N=4.06%, S=18.55% Found C=48.65%; H=5.27%; N=3.93%; S=19.25%

Synthesis of Methyl-(2-N-tosylamino-3-mercapto)propionate

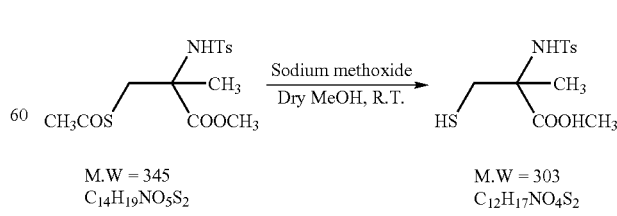

Dry sodium metal (10 mg, 0.43 mmol) was placed in a two necked round bottom flask under nitrogen, then dry methanol (5 ml) was added at room temperature (25° C.)

with stirring. After dissolving all sodium metal, methyl(2-N-tosylamino-3-acetomercapto) propionate (150 mg, 0.43 mmol) was added and the reaction mixture was stirred at room temperature (25° C.) for 6–7 hrs. Methanol was removed under pressure. A colorless oil was obtained, which was purified by column chromatography. The reaction yielded 65.86 mg of product (50%).

Spectral Data

FT IR (CHCl$_3$): 3020; 1738; 1215; 1158; 768; 668 cm$^{-1}$
$^1$H NMR (D$_2$O): δ 7.75 (d, J=8 Hz, 2H); 7.26 (d, J=8 Hz); 5.87 (s, 3H); 3.70 (s, 3H); 3.25 (q, 2H); 2.42 (s, 3H); 2.03 (s, 3H); 1.49 (s, 3H).
$^{13}$C NMR (CDCl$_3$): δ 172.17; 143.35; 139.27; 129.49; 126.92; 66.22; 53.07; 49.39; 22.38; 21.39

Synthesis of 2-Methyl-Cysteine

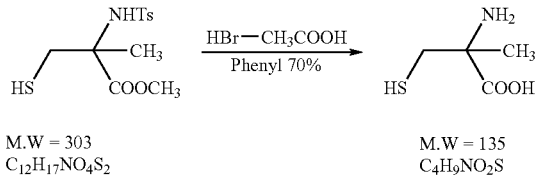

Methyl (2-N-tosylamino-3-mercapto) propionate (100 mg, 0.33 mmol), phenol (94.05 mg, 0.99 mmol), and 10 ml of 32% hydrogen bromide in acetic acid were charged in a thick walled glass tube. It was sealed and heated in a metallic bomb for 12 hours at 80° C. The reaction mixture was allowed to cool to room temperature and then was poured into 60 ml of ether and stirred for 5 min. The ether solution was decanted and the residue was dissolved in 2 ml of water. This aqueous solution was stirred with charcoal and filtered. The filtrate was passed through a Dowex (1×4-50) bed and washed with 3 ml of water. The aqueous solution was concentrated under vacuum at room temperature to obtain 2-methyl cysteine as a sticky mass. The reaction yielded 31.18 mg of product (70%).

Spectral Data

FT IR (nujol): 3615.75; 2542.40; 1611.33; 1511.84 cm$^{-1}$
$^1$H NMR (D$_2$O): δ 3.31 (1H, m-CH$_2$); 2.47 (1H, m-CH$_2$); 1.37 (3H, s-CH$_3$); 1.44 (1H, s-SH).
HPLC (Lichrosphere RP-18): 97.11%

Alternative Synthesis of 2-Methyl-Cysteine

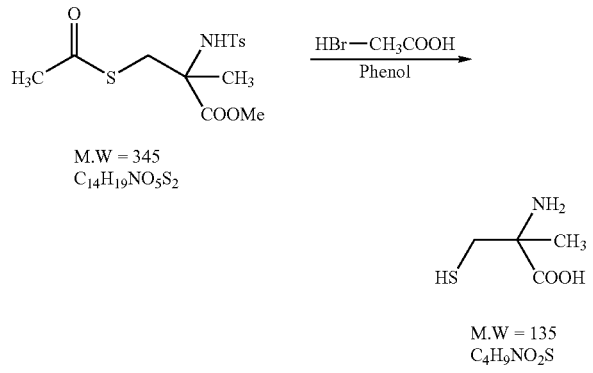

Methyl (2-N-tosylamino-3-mercapto) propionate (100 mg, 0.28 mmol), phenol (81.73 mg, 0.86 mmol), and 10 ml of 32% hydrogen bromide in acetic acid were charged in a thick walled glass tube. It was sealed and heated in a metallic bomb for 12 hours at 80° C. The reaction mixture was allowed to cool to room temperature and then was poured into 60 ml of ether and stirred for 5 min. The ether solution was decanted and the residue was dissolved in 2 ml of water. This aqueous solution was stirred with charcoal and filtered. The filtrate was passed through a Dowex (1×4-50) bed and washed with 3 ml of water. The aqueous solution was concentrated under vacuum at room temperature to obtain 2-methyl cysteine as a sticky mass. The reaction yielded 28.17 mg of product (72%).

Spectral Data

FT IR (nujol): 3615.75; 2542.40; 1611.33; 1511.84 cm$^{-1}$
$^1$H NMR (D$_2$O): δ 3.31 (1H, m-CH$_2$); 2.47 (1H, m-CH$_2$); 1.37 (3H, s-CH$_3$); 1.44 (1H, s-SH).
HPLC (Lichrosphere RP-18): 97.11%

EXAMPLE 8

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a compound represented by Structural Formula (I):

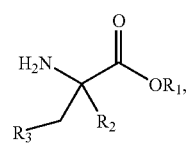

or a salt thereof;
wherein:
R$_1$ is —H or a substituted or unsubstituted alkyl group;
R$_2$ is a substituted or unsubstituted alkyl group;

$R_3$ is —H, —$(CH_2)_xS(CH_2)_yH$, —$(CH_2)_xO(CH_2)_yH$, —$(CH_2)_xNH(CH_2)_yH$, —COOH, —$CONH_2$, —NHC(NH)$NH_2$, a substituted or unsubstituted alkyl group, a substituted or unsubstituted cycloaliphatic group, or a substituted or unsubstituted aromatic group, wherein $R_3$ optionally comprises a protecting group;

x is an integer from 0–12; and y is an integer from 0–4;

comprising the steps of:

a.) reacting the compound represented by Structural Formula (III):

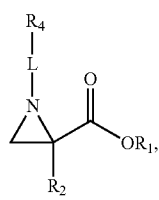

(III)

wherein:

L is a bond, a sulfoxide (—S(O)—), or a sulfone (—S(O)(O)—); and $R_4$ is a substituted or unsubstituted alkyl group or a substituted or unsubstituted aryl group;

with a nucleophile of the formula A-$R_3$, wherein A is —H, —Li, —MgCl, —MgBr, or —MgI, provided that A and $R_3$ are not each —H, and $R_1$, $R_2$ and $R_3$ are as defined above; thereby forming a compound represented by Structural Formula (IV):

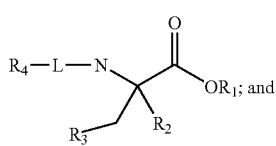

(IV)

b.) cleaving L-$R_4$ and optionally the protecting group of $R_3$ from the compound represented by Structural Formula (IV), thereby forming the compound represented by Structural Formula (I).

2. The method of claim 1, wherein the aziridine represented by Structural Formula (III) is prepared by aziridinating a compound represented by Structural Formula (II):

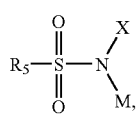

(V)

by reacting said compound with a source of nitrogen and an aziridination catalyst, thereby forming the aziridine represented by Structural Formula (III) where the source of nitrogen is represented by Structural Formula (V):

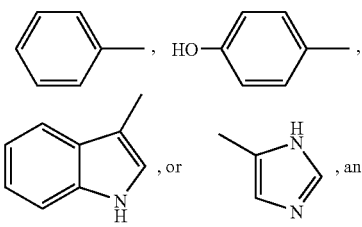

wherein M is an alkali metal, X is a halide, and $R_5$ is a substituted or unsubstituted alkyl group or a substituted or unsubstituted aryl group.

3. The method of claim 2, wherein M is sodium and x is chloride or bromide.

4. The method of claim 2, wherein the aziridination catalyst is a transition metal halide, an alkaline earth metal halide, $Rh_2(acetate)_4$, a dihalogen, phenyltrimethylammonium tribromide, or pyridinium hydrobromide.

5. The method of claim 4, wherein the aziridination catalyst is a copper halide.

6. The method of claim 4, wherein $R_3$ is a —H, —$(CH_2)_x$$S(CH_2)_yH$, —$(CH_2)_xO(CH_2)_yH$, —$(CH_2)_xNH(CH_2)_yH$, —$(CH_2)_xC(O)NH_2$, —$(CH_2)_xC(O)OH$, —$(CH_2)_xNHC(NH)$$NH_2$, a C1–C6 substituted or unsubstituted alkyl group,

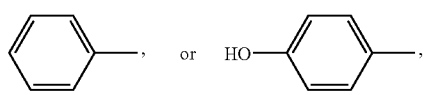

and salts thereof; wherein $R_3$ optionally comprises a protecting group;

x is an integer from 0–6; and y is 0 or 1.

7. The method of claim 6, wherein $R_3$ is —SH.

8. The method of claim 6, further comprising the step of resolving enantiomers or diastereomers of the product of step (b.).

9. The method of claim 8, wherein a (S)-2-amino acid or an ester thereof is isolated from the entantiomers or diastereomers.

10. The method of claim 9, wherein the $R_1$ and $R_2$ are each methyl.

11. The method of claim 1, wherein the aziridine represented by Structural Formula (III) is prepared by aziridinating a compound represented by Structural Formula (II):

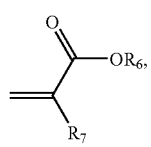

(VII)

by reacting said compound with a source of nitrogen and an aziridination catalyst, thereby forming the aziridine represented by Structural Formula (III) where the $R_1$ and $R_2$ are each methyl, and wherein the source of nitrogen is represented by Structural Formula (V):

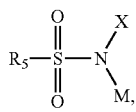

(V)

wherein M is an alkali metal, X is a halide, and $R_5$ is a substituted or unsubstituted alkyl group or a substituted or unsubstituted aryl group.

12. The method of claim 11, wherein M is sodium and X is chloride or bromide.

13. The method of claim 12, wherein the aziridination catalyst is a copper halide.

14. The method of claim 13, wherein $R_3$ is a —H, —$(CH_2)_xS(CH_2)_yH$, —$(CH_2)_xO(CH_2)_yH$, —$(CH_2)_xNH(CH_2)_yH$, —$(CH_2)_xC(O)NH_2$, —$(CH_2)_xC(O)OH$, —$(CH_2)_xNHC(NH)NH_2$, a C1–C6 substituted or unsubstituted alkyl group,

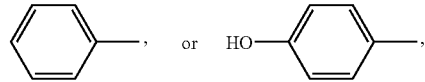

and salts thereof wherein $R_3$ optionally comprises a protecting group;

x is an integer from 0–6; and y is 0 or 1.

15. The method of claim 14, wherein $R_3$ is —SH.

16. The method of claim 15, further comprising the step of resolving enantiomers or diastereomers of the product of step (b.).

17. The method of claim 16, wherein a (S)-2-amino acid is isolated from the enantiomers or diastereomers.

18. The method of claim 1, wherein the aziridine represented by Structural Formula (III) is prepared by aziridinating a compound represented by Structural Formula (II):

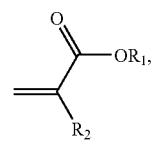

(XVII)

wherein $R_1$ is —H or a substituted or unsubstituted alkyl group, and $R_2$ is a substituted or unsubstituted alkyl group.

19. The method of claim 1, wherein the compound represented by Structural Formula (III) is prepared by reacting an epoxide represented by Structural Formula (IIa):

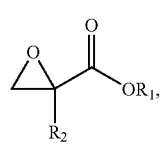

(IIa)

with a nucleophilic nitrogen compound, followed by a hydroxyl activating agent and a base, wherein the nucleophilic nitrogen compound includes a secondary or tertiary nitrogen atom bonded to one or two protecting groups and a substituted phenyl sulfonyl group.

* * * * *

UNITED STATES PATENT AND TRADEMARK OFFICE
CERTIFICATE OF CORRECTION

PATENT NO. : 7,038,073 B2
APPLICATION NO. : 10/439265
DATED : May 2, 2006
INVENTOR(S) : Mukund S. Chorghade, Mukund K. Gurjar and Bhanu M. Chanda It is certified that error appears in the above-identified patent and that said Letters Patent is hereby corrected as shown below:

Claim 2, column 21, line 60 replace 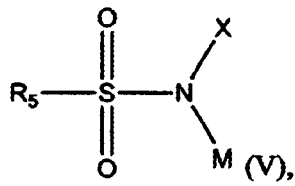

with 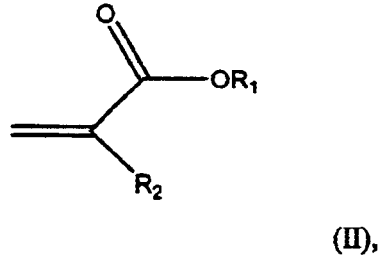

UNITED STATES PATENT AND TRADEMARK OFFICE
CERTIFICATE OF CORRECTION

PATENT NO. : 7,038,073 B2
APPLICATION NO. : 10/439265
DATED : May 2, 2006
INVENTOR(S) : Mukund S. Chorghade, Mukund K. Gurjar and Bhanu M. Chanda It is certified that error appears in the above-identified patent and that said Letters Patent is hereby corrected as shown below:

Claim 2, column 22, line 5 replace 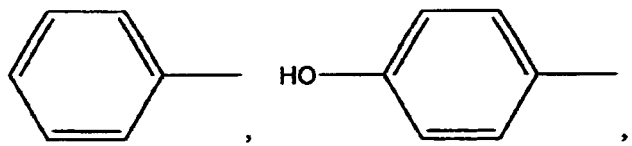

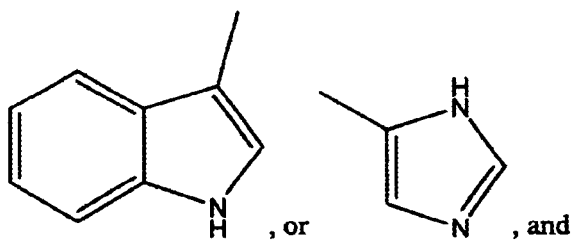

with 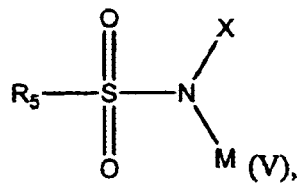

Claim 3, column 22, line 16, delete "x" and insert --X--.

Claim 11, column 22, line 55, replace 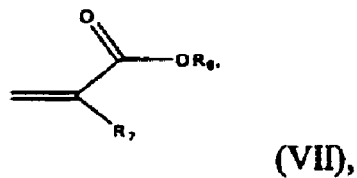

with 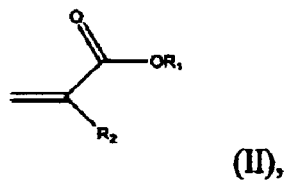

UNITED STATES PATENT AND TRADEMARK OFFICE
CERTIFICATE OF CORRECTION

PATENT NO. : 7,038,073 B2
APPLICATION NO. : 10/439265
DATED : May 2, 2006
INVENTOR(S) : Mukund S. Chorghade, Mukund K. Gurjar and Bhanu M. Chanda It is certified that error appears in the above-identified patent and that said Letters Patent is hereby corrected as shown below:

Claim 18, column 24, line 7, replace

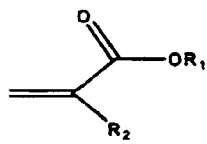   (XVII)

with

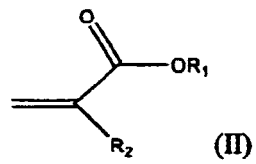   (II)

Signed and Sealed this

Seventeenth Day of October, 2006

JON W. DUDAS
*Director of the United States Patent and Trademark Office*